(12) United States Patent
Gavish

(10) Patent No.: US 9,314,583 B2
(45) Date of Patent: Apr. 19, 2016

(54) SYSTEM AND METHOD FOR INDUCING SLEEP

(71) Applicant: Benjamin Gavish, Eshtaol (IL)

(72) Inventor: Benjamin Gavish, Eshtaol (IL)

(73) Assignee: Yazmonit Ltd., Eshtaol (IL)

( * ) Notice: Subject to any disclaimer, the term of this patent is extended or adjusted under 35 U.S.C. 154(b) by 0 days.

(21) Appl. No.: 14/491,258

(22) Filed: Sep. 19, 2014

(65) Prior Publication Data

US 2015/0367097 A1 Dec. 24, 2015

(30) Foreign Application Priority Data

Jun. 24, 2014 (IL) .......................................... 233353

(51) Int. Cl.
*A61M 21/02* (2006.01)
*A61B 5/0476* (2006.01)
*A61B 5/0205* (2006.01)
*A61B 5/00* (2006.01)
(Continued)

(52) U.S. Cl.
CPC .............. *A61M 21/02* (2013.01); *A61B 5/0205* (2013.01); *A61B 5/0476* (2013.01); *A61B 5/4806* (2013.01); *A61B 5/486* (2013.01); *A61B 5/4812* (2013.01); *A61B 5/4848* (2013.01); *A61M 21/00* (2013.01); *A61B 5/113* (2013.01); *A61M 2021/0022* (2013.01); *A61M 2021/0027* (2013.01); *A61M 2021/0044* (2013.01)

(58) Field of Classification Search
CPC .... A61B 5/1135; A61B 5/486; A61B 5/0022; A61B 5/0205; A61B 5/021

USPC .............. 600/27, 28, 300, 323; 128/897–899, 128/95.1; 601/15
See application file for complete search history.

(56) References Cited

U.S. PATENT DOCUMENTS

| 5,076,281 A | 12/1991 | Gavish |
| 5,167,610 A | 12/1992 | Kitado et al. |
| 5,800,337 A | 9/1998 | Gavish |

(Continued)

OTHER PUBLICATIONS

Gavish B, "Device-guided breathing in the home setting: Technology, performance and clinical outcomes", Biol. Psychol. 2010; 84:150-156.

(Continued)

*Primary Examiner* — Navin Natnithithadha
*Assistant Examiner* — Sunita Reddy
(74) *Attorney, Agent, or Firm* — Peter A. Nieves; Sheehan Phinney Bass & Green PA

(57) ABSTRACT

A system for sleep induction, detecting and tracking includes a monitor for analyzing single- and multiple-respiration patterns of a user and a stimulus generator for providing to the user multiple stimuli each bearing selectable relationships with selected temporal characteristics of the monitored respiration patterns. At least stimulus is operative to change one or more temporal characteristics of the respiration patterns by synchronization of respiration movements with specific aspects of the stimulus. A sync detector determines at least one measure of synchronization between at least one selected temporal characteristic of selected stimuli and a corresponding temporal characteristic of the respiration patterns for selected relationships between the stimuli and the temporal characteristics of the respiration patterns. A sleep detector indicates onset of sleep and a driver continuously controls the operation of the stimulus generator, the sync detector and the sleep detector based on signals as they are received.

31 Claims, 11 Drawing Sheets

(51) Int. Cl.
   *A61M 21/00* (2006.01)
   *A61B 5/113* (2006.01)

(56) References Cited

U.S. PATENT DOCUMENTS

| | | | |
|---|---|---|---|
| 6,662,032 B1* | 12/2003 | Gavish et al. | 600/323 |
| 7,717,858 B2 | 5/2010 | Massad | |
| 8,183,453 B2 | 5/2012 | Wagner | |
| 2004/0116784 A1* | 6/2004 | Gavish | 600/300 |
| 2005/0143617 A1* | 6/2005 | Auphan | 600/26 |
| 2006/0038689 A1 | 2/2006 | Ikegami | |
| 2006/0102171 A1* | 5/2006 | Gavish | 128/95.1 |
| 2007/0203433 A1* | 8/2007 | Murphy | 601/15 |
| 2008/0157956 A1* | 7/2008 | Radivojevic et al. | 340/531 |
| 2008/0319333 A1* | 12/2008 | Gavish et al. | 600/529 |
| 2009/0062598 A1 | 3/2009 | Haisma | |
| 2010/0240945 A1* | 9/2010 | Bikko | 600/28 |
| 2011/0046434 A1* | 2/2011 | Schmeink et al. | 600/27 |
| 2012/0296156 A1* | 11/2012 | Auphan | 600/28 |
| 2013/0066226 A1* | 3/2013 | Baloa Welzien et al. | 600/538 |
| 2013/0190554 A1* | 7/2013 | Vogt et al. | 600/27 |
| 2014/0316192 A1* | 10/2014 | de Zambotti et al. | 600/28 |

OTHER PUBLICATIONS

InterCure Ltd., http://www.resperate.com/, Sep. 18, 2014.
PCT Search Report and Written Opinion for PCT Application No. PCT/IL2015-050626, dated Oct. 22, 2015, 9 pages.

* cited by examiner

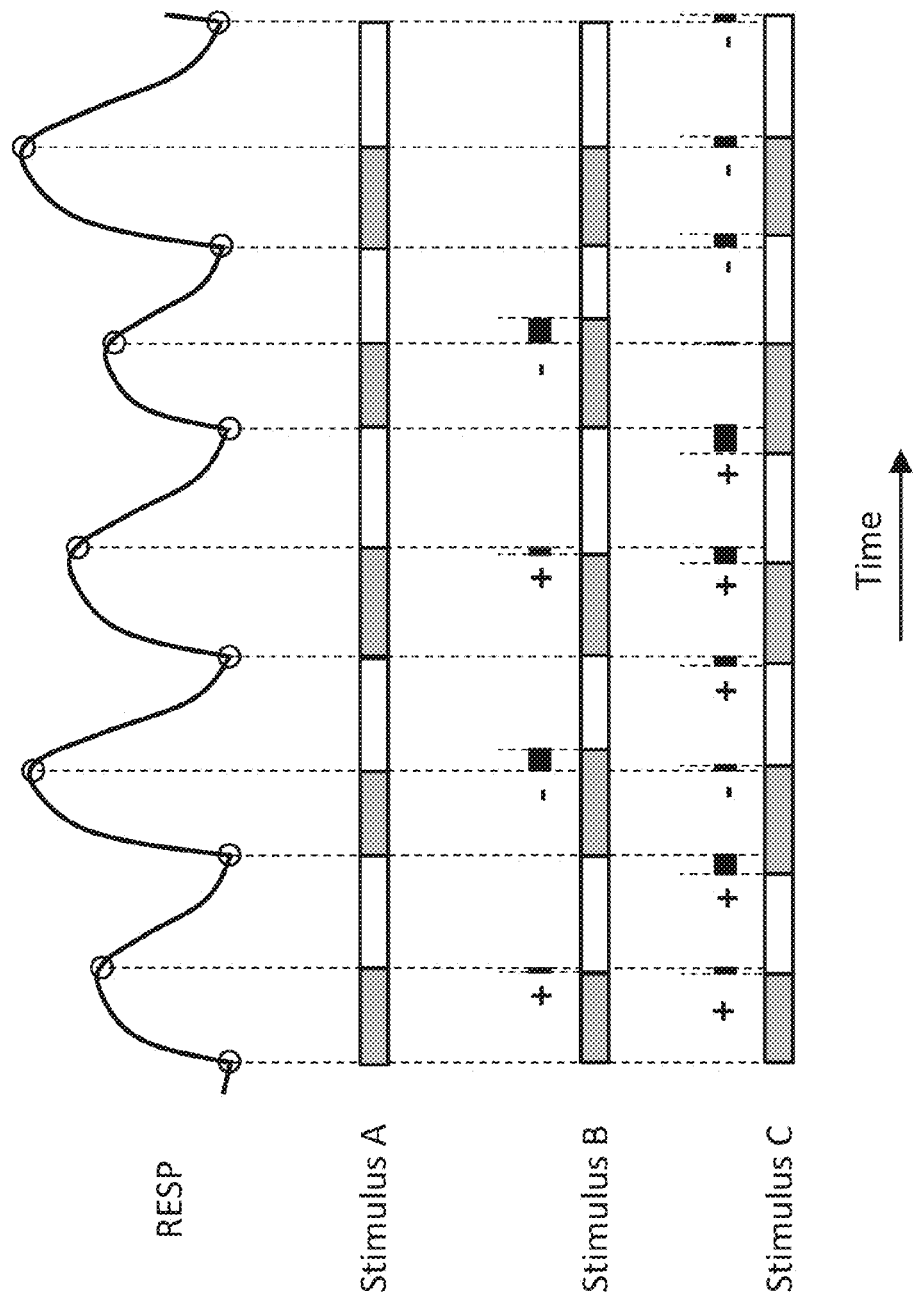

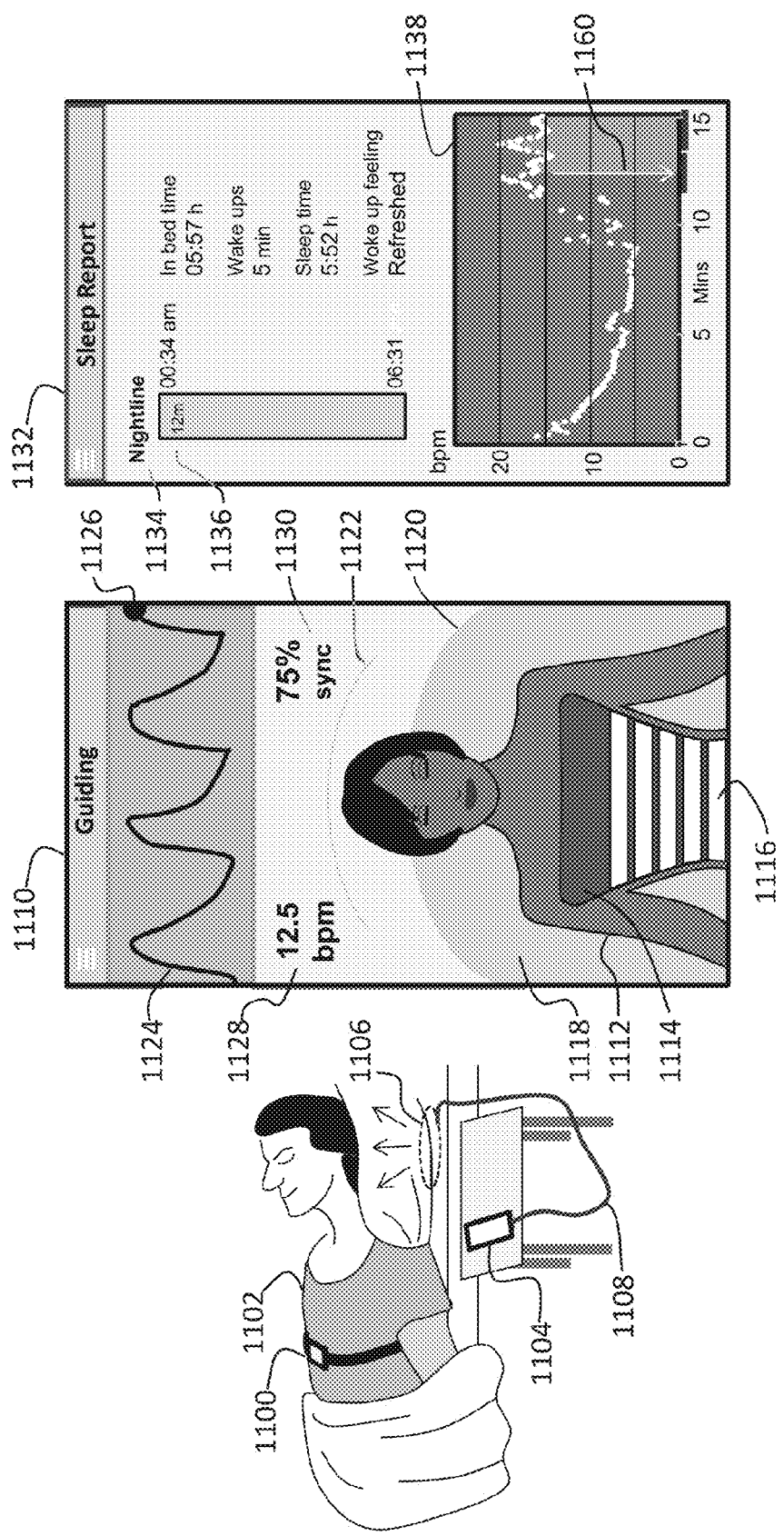

SYSTEM AND METHOD FOR INDUCING SLEEP

FIELD OF THE INVENTION

The present invention generally relates to systems and methods to induce sleep.

BACKGROUND OF THE INVENTION

About one third of the adult population in the USA and other countries experiences frequent difficulty in falling asleep, staying asleep or both, and wakes up unrefreshed despite the opportunity for adequate sleep. Nearly 10% of the US population suffers from chronic sleeplessness, called insomnia. Sleeplessness may result in impaired cognitive, emotional, social and physical functionality during daytime with increased risk for accidents, lower job performance and decreased quality of life. According to analysts, Americans spent over $30 billion in 2012 on sleep-related aids.

Current methods for alleviating the problem include sleep pills, which frequently elicit side effects, improving sleep habits, controlling or eliminating negative thoughts and applying relaxation techniques for stress reduction. However, these do not appear to provide interventions that are efficient in restoring the normal falling-asleep process when disturbed.

The normal falling-asleep process involves progressive disconnection from the environment and decline in control over mental activity and awareness of sensory stimuli. During this process sympathetic neural activity is decreased with resulting muscle tone relaxation; respiration undergoes a series of characteristic variations including respiratory instability, which reflects the intermittency between the different systems that control respiration in the awake and sleep states that changes into highly regular and low-amplitude respiration.

A method and system for sensor-controlled interactive guiding of a user from normal- to slow respiration rates with modified respiration pattern has been described by the present inventor in U.S. Pat. Nos. 5,076,281 and 5,800,337. This technology was implemented in a medical device sold under the name RESPeRATE™ that guides the inspiration and expiration of its user by musical tones, with which the user is requested to synchronize ('sync') breathing movements. The device has been demonstrated to reduce neural sympathetic activity and was cleared by the FDA for treating stress and hypertension. However, the use of that technology for sleep induction is limited by the very process of falling asleep: with increasing drowsiness the user ability to sync breathing movements with a guiding stimulus gradually decreases and the resulting stimulus, now perceived as de-sync, frequently wakes up the user. Furthermore, user awareness regarding the quality of performing the guided respiration is important for achieving outcomes associated with the reduction of sympathetic activity that also includes falling sleep. The prior art discloses neither the detection of the awake-to-sleep transition using a measure for awareness combined with respiration characteristics during guided breathing, nor a strategy for modifying the stimulus after such detection, in a way that would not interfere in the falling-asleep process. In addition, the prior art does not provide a satisfactory real-time continuous measure for the performance quality of guided respiration. Thus, it may be desirable to improve known methods and systems in a way that would extend their applicability to sleep induction and other applications aiming to reduce sympathetic activity.

SUMMARY OF THE INVENTION

The present invention seeks to provide an improved system and method for inducing sleep.

It is an object of the invention to provide a system and method for sleep induction, detection and tracking.

This object is realized in accordance with the invention by a method and system for inducing, detecting and tracking sleep having the features of the respective independent claims.

In accordance with one aspect of the invention there is provided a system for sleep induction, detecting and tracking including:

a monitor for analyzing single- and multiple-respiration patterns of a user;

a stimulus generator for providing to the user multiple stimuli each stimulus bearing selectable relationships with selected temporal characteristics of said single- and multiple-monitored respiration patterns of a user, wherein at least one of said stimuli is operative to change at least one of said temporal characteristics of the respiration patterns by synchronization of respiration movements of the user with specific aspects of said at least one stimulus;

a sync detector that determines at least one measure of synchronization between at least one selected temporal characteristic of selected stimuli and a corresponding temporal characteristic of the respiration patterns for selected time-relationships between the stimuli and the temporal characteristics of the respiration patterns;

a sleep detector responsive to signals provided by the monitor and the sync detector for indicating the onset of sleep; and a driver that is operative to continuously control the operation of the stimulus generator, the sync detector and the sleep detector based on signals as they are received from at least the sync detector, the sleep detector and the monitor.

It will be appreciated that the operator may be different from the user, but for the simplicity of presentation we will use the term 'operator' and 'user' interchangeably.

In accordance with some embodiments the driver controls the events during the system operation from start to end that are organized as phases, referred collectively as 'the session'.

In accordance with some embodiments the system includes a respiration sensor that provides respiration data to a monitor that analyzes continuously these data and identifies in real time or nearly real time those acceptable data that are associated with the known aspects of respiration phases, e.g. inspiration and expiration. Additionally, the monitor determines measures, including single- and multiple pattern characteristics, variability in characteristics between two or more patterns, and trends of characteristics change, where some of these characteristics are temporal measures.

Preferably, after the monitor starts determining the respiration characteristics the driver controls the stimulus generator to provide the user with stimulus pattern having phase durations that are operative to modify one or more phase durations of the corresponding respiration pattern of the user in response to monitored characteristics during the operation of the monitor. It means that the stimulus acts as a respiration guide for a user, who is assumed to be attempting to synchronize voluntarily respiration pattern with the stimulus pattern, as already disclosed in U.S. Pat. Nos. 5,076,281 and 5,800,337. In one mode of implementation of the present invention such respiratory modification involves at least slowing down the respiration rate while prolonging the expiration:inspiration duration ratio.

Preferably, the user awareness to the respiration guiding stimulus is quantified continuously by the sync detector that measures the level of synchronization between the start of specific respiration phase and the start of the corresponding stimulus phase. It is appreciated that the sync level may be one of the indicators for the user quality of performance In accordance with some embodiments the pre-sleep transition, after which the user becomes drowsy, and the onset of sleep are detected, in general, by the sleep detectors typically using combinations of characteristics and trends of respiration and sync that can be distinguished from the ones observed when the user is awake and fully aware of the guiding stimulus.

After sleep detection, the driver changes the temporal relationship between the stimulus and the respiration from a full guiding stimulus that seeks to maintain full synchronization between the stimulus and the respiration to a stimulus that seeks to preserve the user's current sleeping state. We will refer to this stimulus as a "no-guiding" stimulus. Preferably, the transition from "guiding" to "no-guiding" is made in a minimally perceivable way, taking into account that some users can still display some ability to sync at this state. Preferably, in the no-guiding case the stimulus pattern phases may overlay in part the respiration pattern phases. For example, the start of the stimulus inspiration phase may occur upon detecting the start of the inspiration phase, i.e. the stimulus inspiration pattern passively follows respiration inspiration pattern, while the stimulus expiration phase may reflect a moving average of the last-n monitored durations of acceptable expiration phases. It is appreciated that in one extreme case the phases in the no-guiding stimulus pattern overlay the corresponding respiration phases, so the user respiration is unconstrained by the stimulus. In the other extreme all stimulus phases represent moving averages of the corresponding respiration phases, which actually guide a user, who can still shows some ability to sync, towards enhanced respiration stability.

Preferably, after detecting the sleep onset the driver is operative to track the respiration characteristics and their stability and may gradually turn off the stimulus but may also reactivate the guiding or no-guiding type of stimulus so as respectively to induce or maintain sleep, in case the user characteristics indicate a tendency to wake up, thereby assisting in maintaining sleep.

Preferably, some aspects of the driver control over the stimulus generation are subject to the user commands, either in a predetermined way or during the session. For example, the change in respiration characteristics in response to a user-initiated pause in the guiding process enables the driver to enhance personalization of the driving process.

It is appreciated that the various stimulus inputs may be provided to a user individually or simultaneously in multiple forms. Thus for example, an audio stimulus may be combined with a visual and/or tactile stimulus, or two or more audio, visual or tactile stimuli may be provided simultaneously alone or together with other types of stimuli.

Preferably, in one mode of implementation of the present invention the system comprises a belt-type wireless sensor or an under-the-body noncontact sensor that provide the respiration data to a mobile phone; data are processed and stimulus is generated by a mobile application; the user stimulus has the form of musical tones provided to the user via earphones or under-the pillow speakers; the mobile user interface may include also means for observing respiration signal, stimulus, characteristics and providing reports regarding performance, as well as warnings with corrective messages. It is appreciated that the respiration sensor may include any contact or noncontact sensing technology that may enable appropriate determination of the aforementioned characteristics, and where the sensor signal can be provided through wire or wirelessly. It is further appreciated that the system may also be standalone or has the form of an application for laptop, iPAD™ or other forms of a digital system that includes processing of sensor output and capability to generate the said multimedia stimulus. iPAD is a trademark of Apple Inc., Cupertino, Calif., USA.

There is additionally provided in accordance with another aspect of the invention a method for sleep induction, detection and tracking comprising:

monitoring and analyzing monitored single- and multiple-respiration patterns of a user;

providing to the user multiple controllable stimuli each bearing selectable time-relationships with selected temporal characteristics of said single- and multiple-monitored respiration patterns, where at least one of said time-relationships is operative to change at least one of said temporal characteristics of the respiration patterns during the respiration analysis by synchronization of respiration movements of the user with specific aspects of the stimuli;

determining at least one measure of synchronization between at least one selected aspect of selected stimuli and a corresponding temporal characteristic of the respiration patterns;

detecting the onset of sleep based on said monitored respiration patterns and the at least one measure of synchronization; and continuously controlling the stimuli based on respective current signals relating to at least the at least one measure of synchronization, detection of onset of sleep and the monitored respiration patterns.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 10 is an annotated illustration of a typical respiration signal with three examples of non-guiding stimuli having different temporal relationships with the respiration signal in accordance with an embodiment of the invention;

FIG. 11a is an illustration of a user with the system in accordance with one of the best modes of implementation of the invention; and FIGS. 11b and 11c are illustrations of embodiments of mobile-phone screens in accordance with an implementation of the invention.

DETAILED DESCRIPTION OF EMBODIMENTS

Figure 1:
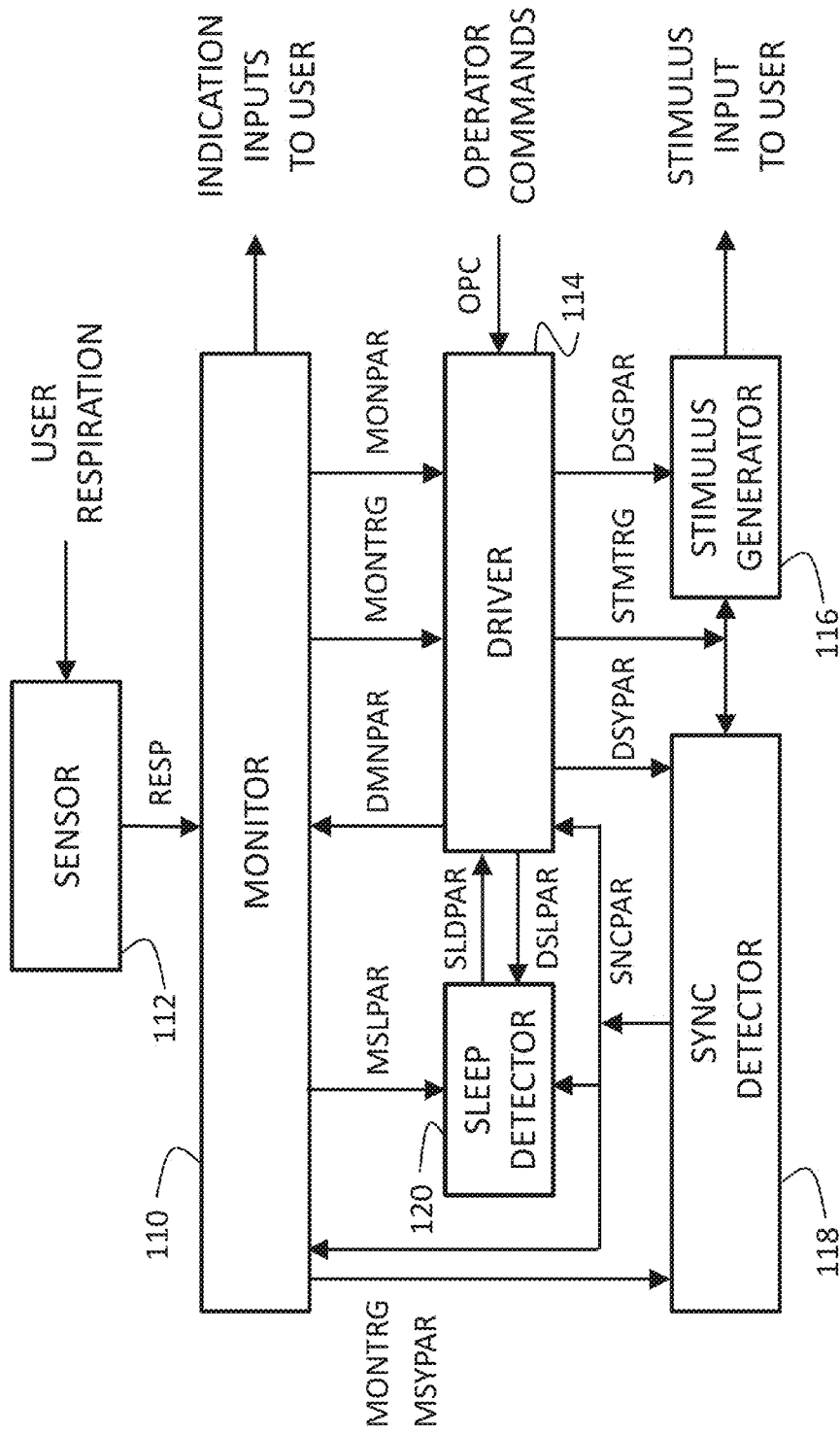
FIG. 1 is a simplified block diagram illustration of a system for sleep induction constructed and operative in accordance with an embodiment of the invention.

Reference is now made to FIG. 1, which is a simplified block diagram illustration of a system 100 for sleep induction constructed and operative in accordance with a preferred embodiment of the present invention.

The system 100 preferably comprises a monitor 110 for analyzing respiration of a user. The respiration signal RESP in continuous or digitized form is generated by a respiration sensor 112. The operation of monitor 110 is principally to analyze the respiration signal, RESP and generate output signals MONPAR representing characteristics of a single or multiple respiration patterns; a trigger signal MONTRG representing the timing of the respiration pattern components, for example, the onset of inhale and exhale movements. MONPAR includes also signals MSYPAR that mark acceptability of some characteristics as representing respiration patterns and signals MSLPAR that express trends of multiple-pattern characteristics—both provided to other modules of the system. In the context of the present invention the term "trend" relates to a measure for the direction of change of a given variable over time or along a sequence of patterns.

In accordance with some embodiments of the present invention, there is further provided a driver 114 that controls, in general, the structure of a session performed by the user that includes a number of phases. Some phases are predetermined and the occurrence of others depends on inputs generated during the session and command provided by the user. Most of the session phases are characterized by specific temporal relationships between selected characteristics of the stimulus and the user respiration patterns. In accordance with some embodiments of the invention, the driver 114 is responsive to operator commands input, collectively referred to as OPC, which may provide by the user or by an 'operator', e.g. a health professional.

The driver 114 indicates to the monitor 110 the session phase via the signal DMNPAR, receives in return the signals MONPAR and MONTRG, and in response feeds to a stimulus generator 116 an array of signals DSGPAR that defines the stimulus characteristics, and a timing signal STMTRG that marks the stimulus timing.

Some of the temporal relationships between the stimulus and the respiration patterns are determined by the driver 114 in response to changes in the characteristics of the respiration pattern provided by the monitor 110 during the operation of the monitor 110; the level of synchronization between selected characteristics of the stimulus and respiration, which is provided by a sync detector 118 via the variable SNCPAR, and the variable SLDPAR that indicates sleep provided by a sleep detector 120. The driver controls the operation of the sync detector 118 and the sleep detector 120 according to the session phase, as indicated by the variables DSYPAR and DSLPAR, respectively.

The stimulus generator 116 is operative to provide to the user a stimulus input bearing selectable relationships with temporal characteristics of the respiration patterns, where the selection is determined by the driver 114 and at least one of these relationships means providing to the user a stimulus input that is operative to change at least one of the temporal characteristics of the respiration pattern of the user provided by sensor 112. It is appreciated that in this case the user is requested to synchronize the aforementioned characteristic in the respiration pattern with the corresponding characteristic in the stimulus pattern, which leads to the perception of the stimulus by the user as a respiration guide.

The sync detector 118 determines for each respiration pattern the level of synchronization between the onset timing of a specific respiration phase MONTRG indicated by the monitor 110 and the onset timing of the corresponding stimulus phase STMTRG indicated by the driver 114, provided that the respiration pattern is found acceptable by the monitor 110, as notified by the signal MSYPAR. In accordance with some embodiments the level of synchronization is taken as a measure for the user awareness to the respiration guiding stimulus. The operation of the sync detector varies according to the session phase, as indicated by the driver 114 via the signal DSYPAR. The sync-related measures SNCPAR determined for single- and multiple respiration patterns are provided to the monitor 110, the driver 114, and the sleep detector 120.

The sleep detector 120 indicates the onset of sleep by providing the driver 114 with the signal SLDPAR, which is determined using the signals MSLPAR provided by the monitor 110 and SNCPAR provided by the sync detector 118.

It is to be noted that the sync detector 118 and the sleep detector 120 and their relationship with each other and with the monitor 110 and the driver 114 are distinguished from the prior art.

Figure 2:
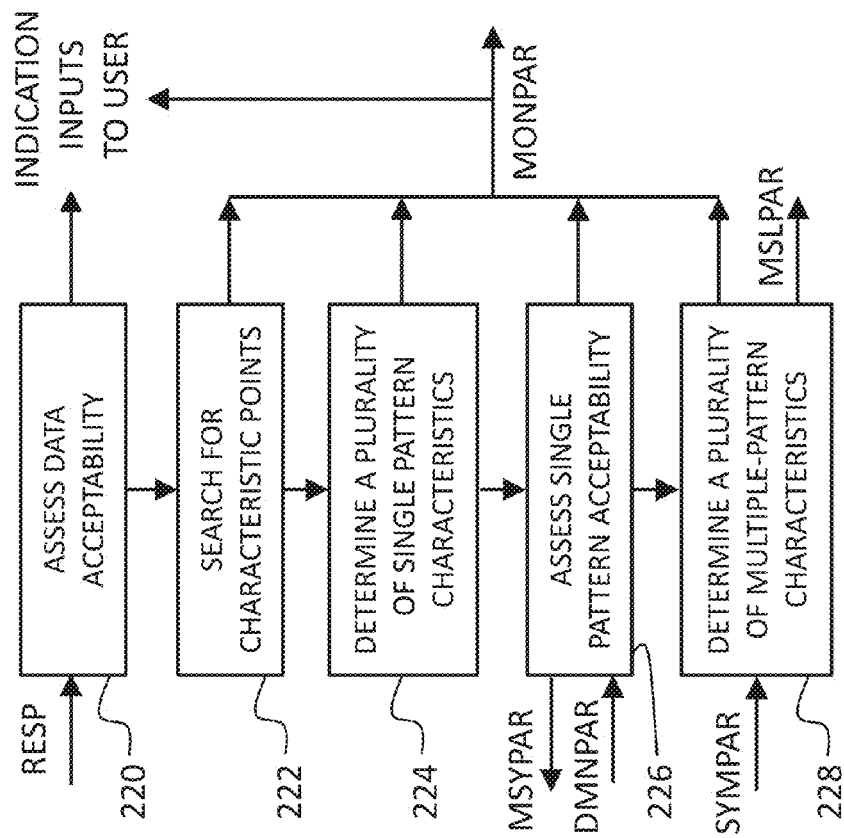
FIG. 2 is a flowchart illustrating operation of a monitor employed in the system of FIG. 1.

Reference is now made to FIG. 2, which is a flowchart of an embodiment illustrating the operation of a monitor employed in the system of FIG. 1. The respiration data RESP provided by the respiration sensor 112 are subjected to analysis that includes determining the data acceptability, i.e. being within predetermined range (procedure 220); searching for characteristic points (procedure 222) that enables to calculate single pattern characteristics (procedure 224) and assessing its acceptability as a respiration pattern (procedure 226); determining a plurality of multiple-pattern characteristics (procedure 228). The outcomes of procedures 222-228 are provided to the monitor 114, the sync detector 118, the sleep detector 120 and the user (FIG. 1). More details about the various procedures, in accordance with the present invention, are provided hereafter. It is to be noted that the pattern analysis employed in the present invention goes beyond that described in U.S. Pat. Nos. 5,076,281 and 5,800,337. It is further appreciated that in one mode of implementation of the present invention, which includes a wireless sensor, the monitor 110 also provides indications for the status of pairing and connectivity of the sensor to the system.

Figure 3:
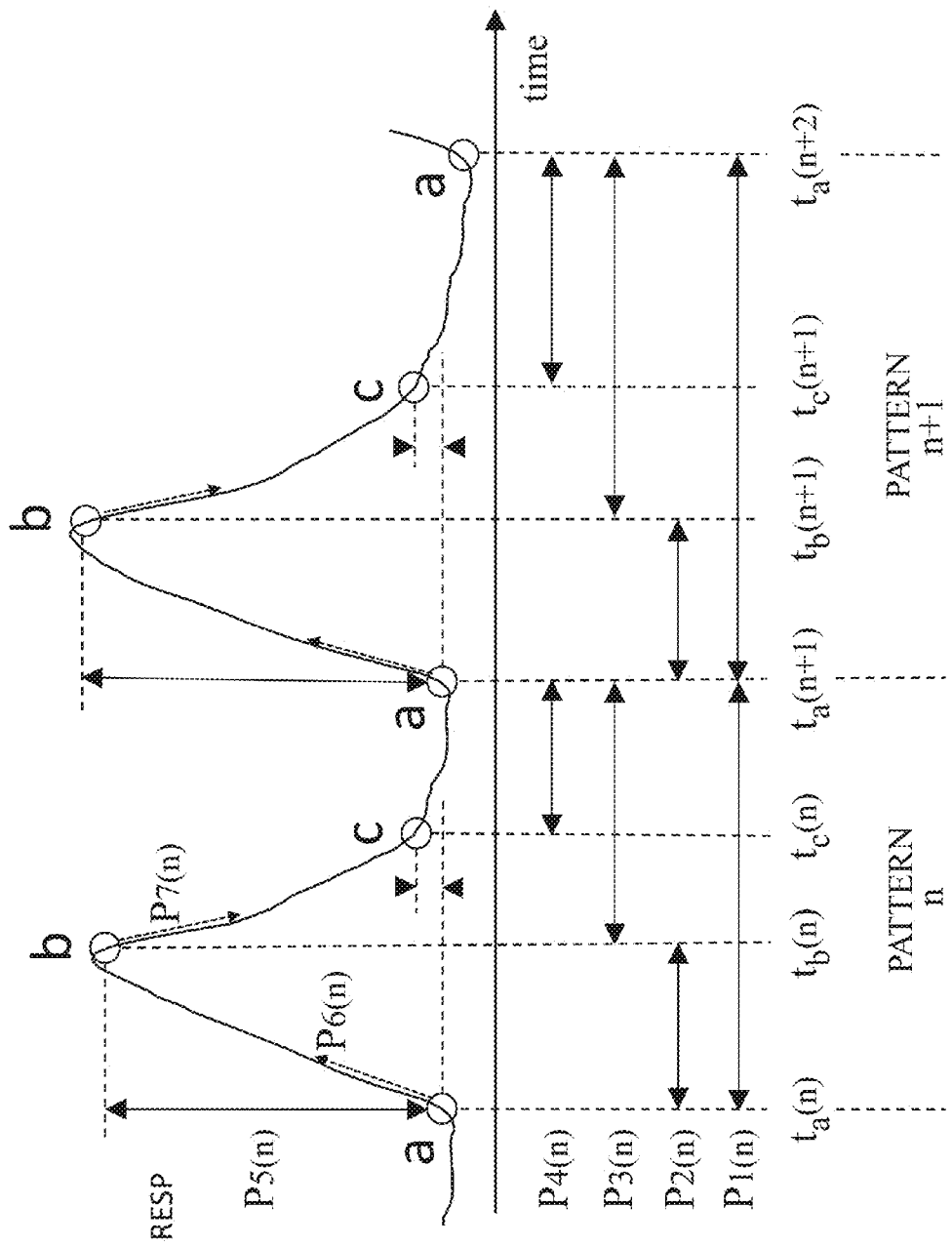
FIG. 3 is an annotated illustration of a typical raw respiration signal provided by the sensor and typical single-pattern characteristics provided by the monitor in accordance with an embodiment of the invention.

The search for characteristic points by procedure 222 is described with reference to FIG. 3 that illustrates a recorded sample of a typical respiration signal RESP sensed by a belt-type respiration sensor, as described in U.S. Pat. No. 7,717,858, plotted as a function of time. The RESP signal contains a number of characteristic points employed by the present invention. Preferably, most or all of the characteristic points are detected in real time using methods known in the art. The detection of some characteristic points may require storage of the RESP signal for near real-time analysis. The preferred characteristic points mark the onsets of inspiration (point a), exhalation (point b) and the post expiratory pause (point c) that define functionally distinguishable phases in the respiration pattern. The detection times of points a, b and c that belong to the $n^{th}$ pattern are marked by ta(n), tb(n) and tc(n), respectively. Upon detecting each of these characteristic points, procedure 222 generates a trigger MONTRG provided to both the driver 114 and the sync detector 118 (FIG. 1). Other types of characteristic points are found in prior art, for example, in U.S. Pat. No. 5,800,337. It is appreciated that the respiration data RESP and the variables used in process of detection may be provided to the driver as part of the MONPAR and be displayed to the user.

The stored characteristic points are then used by procedure 224 for determining a plurality of single pattern characteristics that establish part of the signals MONPAR provided by the monitor 110 to the driver 114 (FIG. 1). Examples for the single pattern characteristics, preferably calculated in real time, include the following (FIG. 3):

P1($n$) Respiration period T defined by the time interval between points 'a' that belong to patterns n and n+1, i.e. ta(n+1)−ta(n). Given T (in sec) the corresponding respiration rate RR (in breaths/min) is equal to 60/T.

P2($n$) Inspiration time Tin defined by the time interval between points a and b in pattern n, i.e. tb(n)−ta(n).

P3($n$) Expiration time Tex defined by the time interval between point b in pattern n and point a in pattern n+1, i.e. ta(n+1)−tb(n).

By definition P1($n$) equals P2($n$)+P3($n$), i.e. T=Tin+Tex.

P4($n$) Post expiratory pause Tpex defined by the time interval between point c in pattern n and point a in pattern n+1, i.e. ta(n+1)−tc(n).

P5($n$) Respiration amplitude AMP is defined by the difference in the signal level between points a and b in pattern n.

P6($n$) and P7($n$) are, respectively, the initial slopes for inspiration (at point a) and expiration (at point b) in pattern n.

Point c may be detected in real time by finding the time at which RESP level is higher than that of point a by a given fraction of AMP, e.g. 10%.

Additional characteristics may include relationships between the above-mentioned variables as well as any other suitable variables. Information relating to the characteristic points, including their location relative to the onset of the pattern and other characteristic points is stored.

In accordance with some embodiments, acceptability of a detected signal pattern as a respiration pattern is assessed by procedure 226, which compares characteristics with thresholds, the RESP signal and the mutual relationships over time of some of the characteristics are determined by routine 224. Such thresholds are preferably specific to the phase of operation received from the driver 114 via signal DMNPAR (FIG. 1) and may be predetermined or obtained adaptively via statistical analysis of previous characteristics during a session phase, e.g. using upper/lower 5% values. The use of slopes P6($n$) and P7($n$) (FIG. 3) with adaptive thresholds enables detection and exclusion of low amplitude respiration patterns and some artifacts in real time that are prevalent during sleep. It is to be noted that this aspect has not been disclosed in the aforementioned prior art.

Procedure 226 also provides indication for the pattern acceptability to the driver 114 via the signal MONPAR, to the sync detector 118 via the signal MSYPAR and to the user (FIG. 1) preferably in audiovisual form with proposed corrective action.

The characteristics of acceptable patterns are then used by procedure 228 for the determination of multiple-pattern characteristics. These include, but are not limited to, the following aspects or combinations thereof including, moving averages of single- or multiple pattern characteristic; trends; variability between two successive characteristics in a continuous or dichotomous form; variability within multiple successive patterns, preferably estimated by standard deviation, and variables characterizing recurrent groups of multiple-patterns, e.g. periodic- or Cheyne-Stokes respiration. It is to be noted that the last two aspects are not disclosed in the aforementioned prior art. Some of the multiple-pattern characteristics are provided to the sleep detector 118 via MSLPAR. Respiration irregularity may be quantified as moving average of variability measures and may be provided to the driver 114 together with error indications for an isolated series of respiration patterns that cannot be interpreted as normal respiration, as sudden change in the body position, coughing, hiccups, yawning, chatting etc. that require comparison of some specific characteristics with adaptive thresholds.

Procedure 228 also generates measures for quantifying the performance of the user that preferably relates to the ability of the user to sync respiratory movements with the stimulus, breathing slowly and doing it for a long enough period of time. Such measures may include the single-pattern characteristic SNCPAR provided by the sync detector 118 (FIG. 1) and also its combination with another desired single-pattern characteristics, e.g. respiration rate. An example for a related measure is the accumulated time spent in breathing slower than 10 breaths/min with sync greater than a predetermined threshold. Other overall preferable performance measures may be the percentage of time spent in irregular breathing or percentage of unacceptable respiration patterns calculated over a predetermined window of time or a given number of detected patterns and may be provided to the user as indications for errors together with corrective actions. It is to be noted that sync-based performance measures are not disclosed in the aforementioned prior art.

As illustrated in FIG. 2, at every stage of the operation different variables, such as respiration data and error messages, may be displayed to the user as indication inputs, thereby allowing the user to control all steps of the operation by appropriate commands (FIG. 1).

Figure 4:
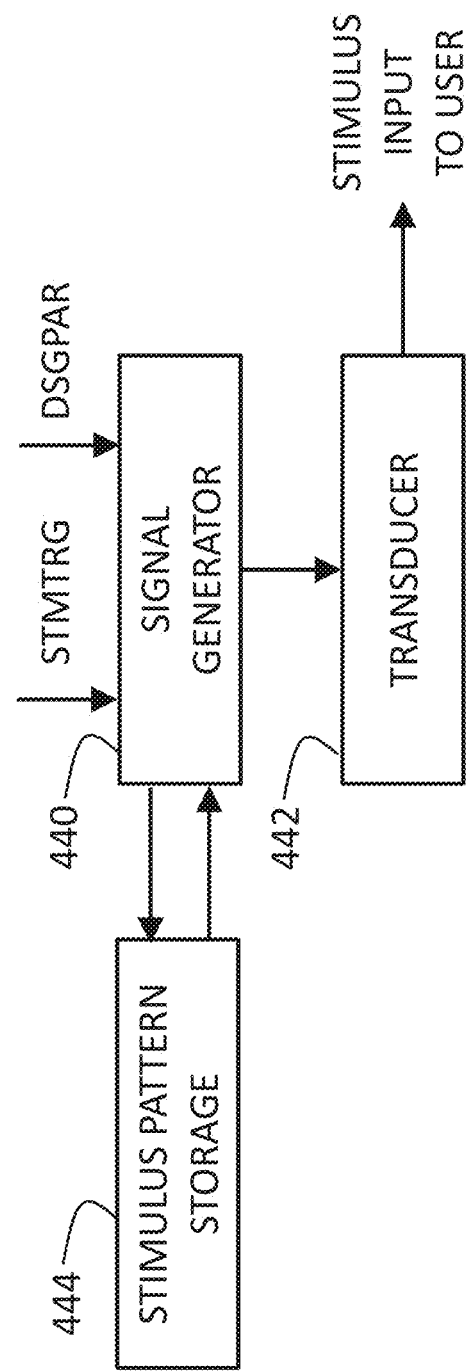
FIG. 4 is a block diagram illustrating operation of a stimulus generator employed in the system of FIG. 1.

Reference is now made to FIG. 4, which is a flowchart of an embodiment illustrating the general structure of a stimulus generator 116 employed in the system of FIG. 1, comprising a signal generator 440 that generates signals in the form of electrical signals or digital codes that when provided to a transducer 442 are converted thereby into a desired stimulus that is fed to the user. The process is controlled by variables provided by the driver 114 (FIG. 1) of the types STMTRG and DSGPAR, corresponding respectively to the timing of the stimulus onset and characteristics of the stimulus pattern. DSGPAR may also include a command to change with time the stimulus intensity and turn on and off the stimulus generation. The coded characteristics of the various stimuli to be generated are stored in a stimulus pattern storage 444 that communicates bi-directionally with the signal generator 440. In one embodiment musical stimuli generated and DSGPAR may indicate the generating sequence of musical notes with prescribed duration, musical instruments, relative sound intensity and other multiple musical characteristics that depend of the sound generation technique, e.g. wavetable synthesis. The temporal extension of a stimulus may start from a time point marked by a trigger STMTRG and end according to an indication provided by the driver 114 via DRVTRG. In such an embodiment, the transducer may include an amplifier and speaker. The stimulus generator 116 may also provide stimuli with randomness that can be applied to both the structure of the music and the duration of specific parts of the music or recorded sounds like sea waves, where both options can be controlled by the driver 114 via STMTRG and DSGPAR with appropriate recordings stored by the stimulus pattern storage 444. The stimulus generator 116 may be operated to generate also visual, pressure, vibration, electrical, thermal and any other desired stimulus. More details with reference to specific stimuli are provided in the prior art, specifically in U.S. Pat. Nos. 5,800,337 and 8,183,453.

In some phases of the session the user is requested to synchronize the onset of specific respiration phases to the corresponding stimulus phases. However, the ability of the user to do this decreases gradually during the process of falling asleep, as a natural consequence of the reducing awareness to external stimuli, in addition to other sources of sync reduction as defocusing and the potential difficulty of following the stimulus guidance to low respiration rates. This situation favors a procedure for measuring sync in real time for selected characteristic points of each respiration pattern as a measure for the user awareness.

Figure 5:
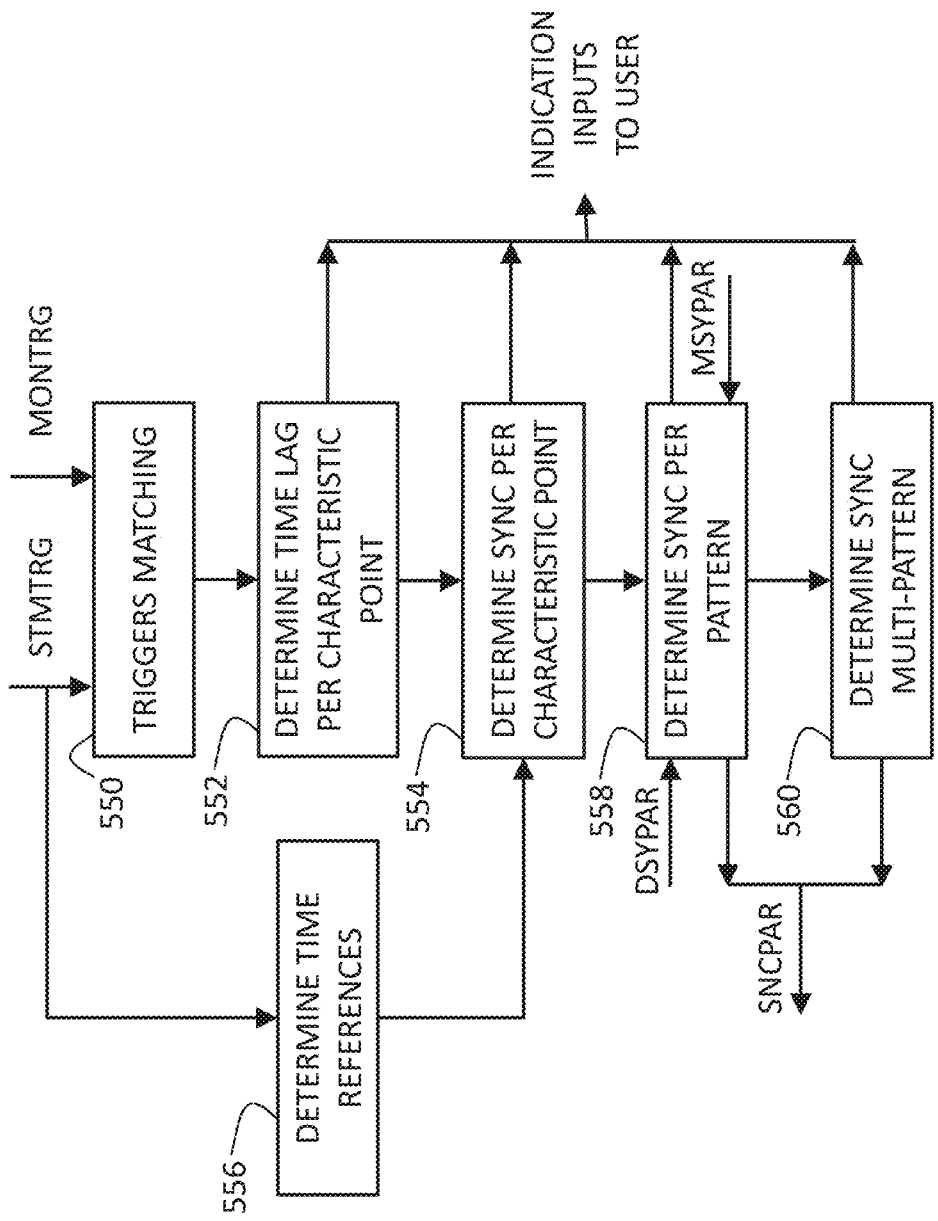
FIG. 5 is a block diagram illustrating operation of a sync detector employed in the system of FIG. 1.
Figure 6:
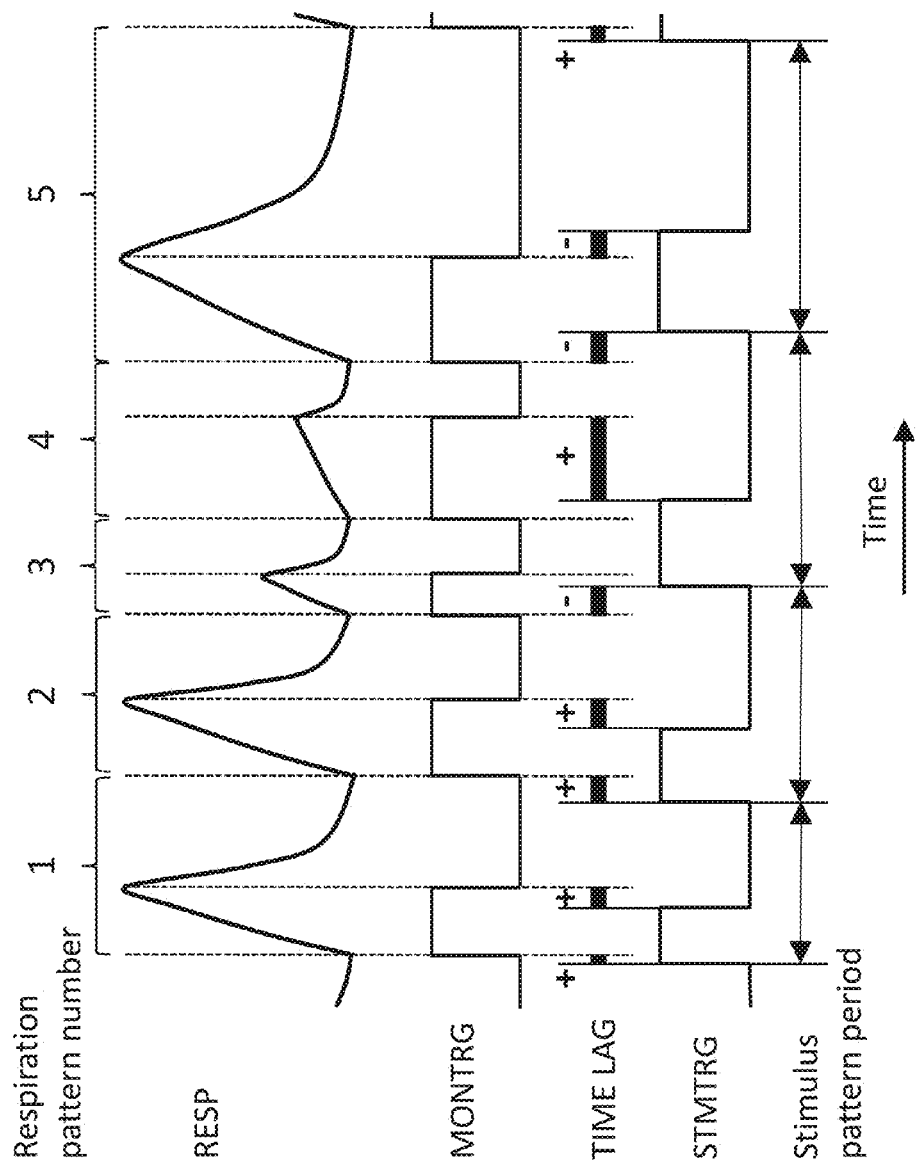
FIG. 6 is an annotated illustration of a typical respiration signal with an example of triggers marking the detection time of characteristic points, the timing of the stimuli applied to the user, and the time lag between these triggers in accordance with an embodiment of the invention.

Reference is now made to FIG. 5, which is a flowchart of an embodiment illustrating the operation of the sync detector 118 employed in the system of FIG. 1, comprising a trigger matching unit 550 that receives from the monitor 110 (FIG. 1) a trigger signal MONTRG that marks the detection time of characteristic points (FIG. 3) and receives from the driver 114 a trigger signal STMTRG that marks the timing of the corresponding stimuli to the user (FIG. 1). Typical forms of MONTRG and STMTRG signals based on the inspiration and expiration phases that correspond, respectively, to onsets at points 'a' and 'b' in FIG. 3, are illustrated in FIG. 6. The trigger-matching unit 550 assesses the validity of one-to-one correspondence between events marked by MONTRG and those marked by STMTRG. Characteristic points, for which such matching is not possible, are marked and excluded from the sync detection process at a later stage. In the example illustrated in FIG. 6 the inspiration and expiration phases are represented, respectively, by the high- and low MONTRG levels. The stimulus pattern may include, for example, a high-pitch 'inspiration' tone and a low-pitch 'expiration' tone that correspond, respectively, to the high and low STMTRG levels with which the user is requested to sync inspiration and expiration. Respiration patterns 1, 2 and 5 have matching stimulus patterns by mean of events order, i.e. the onsets of the inspiration movement and tone are next to each other. The same is true for the expiration movement and the tone. Such matching does not occur for the expiration movement in pattern 3 and for the inspiration in pattern 4. It is to be noted that the principles of trigger matching described here are meaningful for any number of characteristic points that can be defined on the respiration pattern in real time or nearly real time with corresponding aspects in the stimulus pattern.

Procedure 552 determines for each characteristic point the time lag between the onsets of each of the corresponding phases in the respiration and stimulus patterns with validated trigger matching. This time lag may be defined as positive if the respiration phase onset lags after the stimulus phase onset and negative otherwise (FIG. 6). The time lag can be used by procedure 554 as a measure for the sync per characteristic point by means of the deviation in the start of a respiration phase from the timing of the corresponding stimulus. Alternatively or additionally, procedure 556 determines from STMTRG time references with which the time lag can be compared, e.g. the stimulus pattern period shown in FIG. 6. Another example may be the duration of the stimulus phase associated with the relevant characteristic points. Using the time references, procedure 554 preferably expresses the sync per characteristic point as a function of the ratio between the time lag and the phase duration or the stimulus period or any other appropriate time reference.

Procedure 558 determines the sync per pattern, as represented by the time lag in absolute or relative form using the time references for one representative phase, or as simple or weighted average for selected characteristic points in a pattern. Such measure may exclude patterns that were found unacceptable as respiration pattern, e.g. pattern 4 in FIG. 6, as indicated by input MSYPAR provided by the monitor 110 (FIG. 1) and respiration patterns that could not be matched by the stimulus patterns, e.g. pattern 3 in FIG. 6. Sync can also be expressed as a categorical variable by providing thresholds for the time lag in its absolute or relative form, e.g. sync is 1 if the averaged the absolute value of the sync per pattern time or inspiration onset is smaller than 20%, and zero elsewhere. Such thresholds may depend on the session phase in a way provided by the driver 114 (FIG. 1) via DSYPAR. These indications can also inactivate the procedure 558 for some modes of operation, for which sync determination is not meaningful. Procedure 558 provides the monitor 110 via SNCPAR (FIG. 1) the sync measure per pattern for further analysis.

Procedure 560 determines sync over multiple patterns by means of moving averages, trends and variability and provides one or more of the resulting characteristics to the monitor 110, the driver 114 and the sleep detector 120 via SNCPAR (FIG. 1).

The sync per characteristic points, per pattern and for some of its multiple-pattern expressions is provided to the user as performance indicators for the user ability to sync respiration with the stimulus and as an expression of awareness. It will be appreciated that other or additional procedures can be used, if appropriate, in expressing sync real time or nearly real time.

It is further to be noted that in the aforementioned prior art, the sync detector is based on the time shift between an onset of corresponding characteristic points in the respiration and the stimulus, such that if it becomes large enough, the sync detector activates a procedure for correcting it by modifying the stimulus. This is distinguished from the present invention where the sync is measured continuously and provides important information about awareness and performance that is lost in the aforementioned prior art where the shift is corrected.

Figure 7:
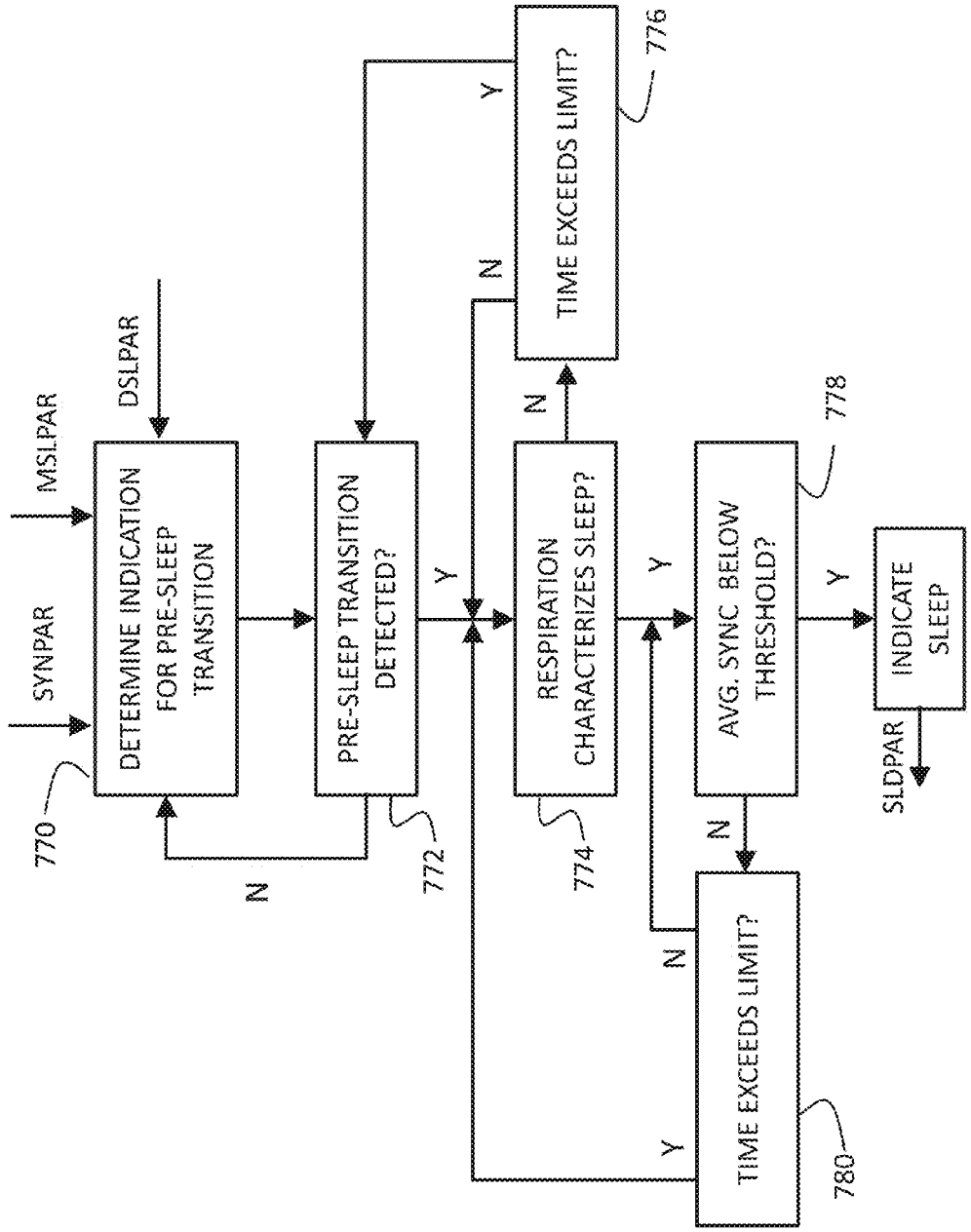
FIG. 7 is a flowchart illustrating operation of a sleep detector employed in the system of FIG. 1.

Reference is now made to FIG. 7, which is a flowchart illustrating the operation of the sleep detector 120 employed in the system of FIG. 1. This procedure is based on the physiological picture of the falling asleep process but includes the unique feature of attempting to synchronize the respiration pattern with a stimulus pattern that induces sleep via respiratory pattern modification, preferably according to the technology described in U.S. Pat. No. 5,076,281 and U.S. Pat. No. 5,800,337, but not doing so when the dissociation from the environment is high enough. The sleep detector 120 comprises a procedure 770 that receives the signals MSLPAR and SNCPAR from the monitor 110 and the sync detector 118 (FIG. 1) that includes in some embodiments moving averages of respiration characteristics and sync, respectively. Procedure 770 is turned on and off by the commands DSLPAR provided by the driver 114 (FIG. 1). In general, procedure 770 calculates preferably for each new respiration pattern the trends for selected characteristics that are known to undergo simultaneously typical changes before a subject falls asleep and determines a score that peaks when all selected trends display the desired trend and/or level of the characteristics in the most pronounced manner. The decision statement 772 expresses the search for the onset of the pre-sleep transition at the time point, in which the score exceeds a known threshold.

The decision statement 774 expresses the search for a combination of respiration characteristics that characterizes sleep. This may naturally happen at the end of the pre-sleep transition. However, if the user does not display sleep-related respiration within a predetermined time limit, as requires by the decision statement 776, the search for the onset of a pre-sleep is renewed. In case the user does display sleep type of respiration within the time limit, the decision statement 778 searches for the time, in which the moving average of sync falls below a predetermined threshold that indicates a low-enough level of awareness that causes the user to fail in synchronizing respiration movements with the stimulus. If such an event is not detected within a predetermined time limit, as required by the decision statement 780, it means that the user may be deeply relaxed and displays sleep-like respiration, but is not asleep. In this case, the process returns to the point of assessing sleep-related respiration. However, if the moving average of sync falls below a predetermined threshold the user is indicated as asleep. This time point of falling asleep is provided to the driver 114 (FIG. 1) via signal SLD-PAR. It will be appreciated that the present description of the sleep detector operation can be generalized to a series of consecutive phases wherein the end of each phase depends, in general, on measures describing trends and moving averages of phase-specific selected characteristics and is subject to time limits.

Figure 8:
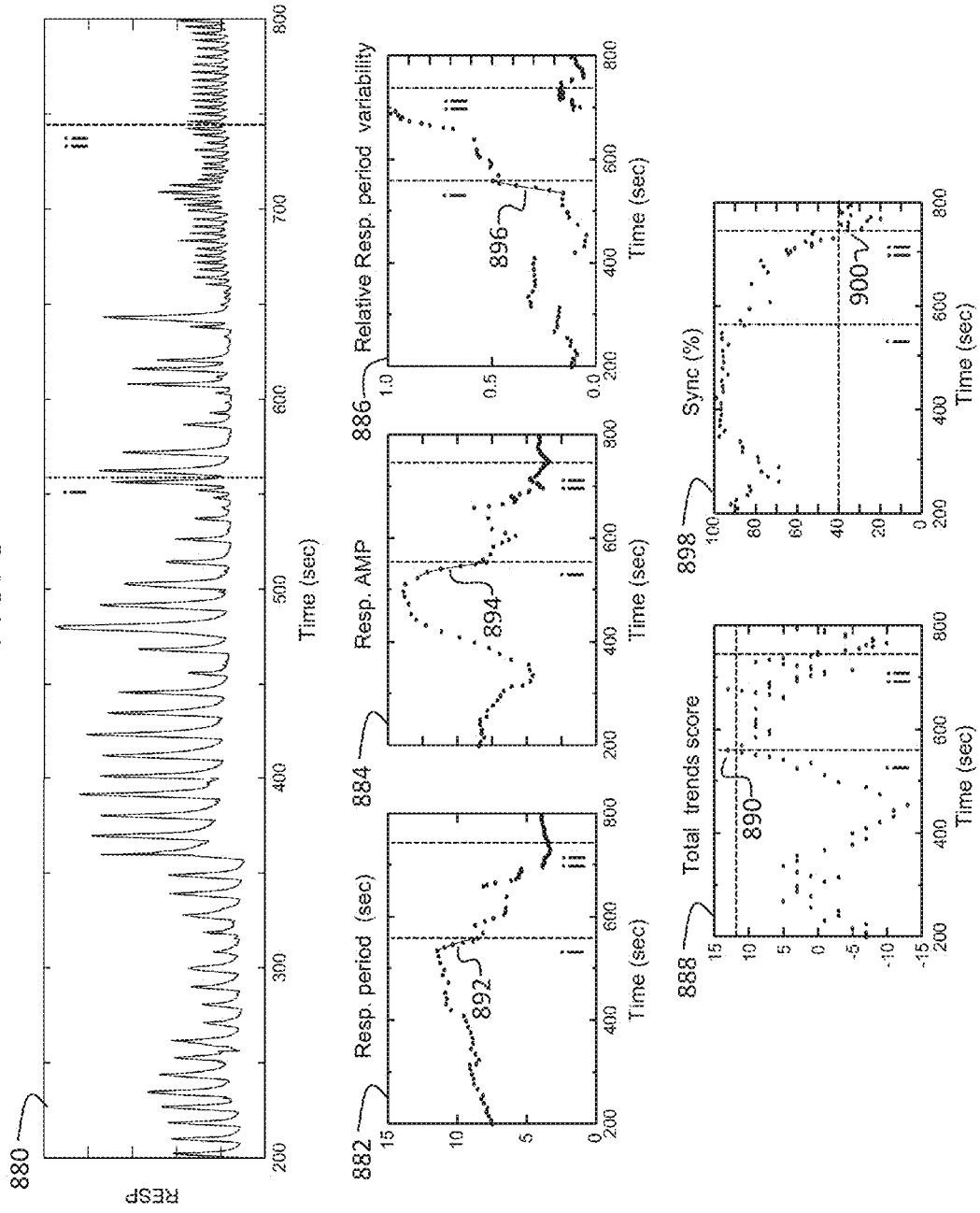
FIG. 8 is an illustration of the time variation of variables involved in a typical process of the sleep detection described in FIG. 7 in accordance with an embodiment of the invention.

Reference is now made to FIG. 8 that illustrates typical data processing performed by the sleep detector 120 (FIG. 1) in one implementation of the present invention using real data. The method was applied to a user, who was initially awake but fell asleep during the depicted time window. Frame 880 shows a record of the respiration signal RESP during 10 minutes (not starting at the beginning of the session), where the stimulus in the present data range consists of musical tones guiding inspiration and expiration towards slows breathing with a relatively prolonged expiration, as conducted by the RESPeRATE™ device following the description given in U.S. Pat. No. 5,800,337. Respiration displays a gradual increase in the respiration period, i.e. decrease in the respiration rate, until about 550 sec, where respiration starts showing a typical pre-sleep irregular pattern in terms of both period and amplitude AMP with a general tendency of shortening the respiration period until about 670 sec, where respiration becomes regular, with shorter period and lower amplitude, i.e. respiration becomes faster and shallower. Frames 882, 884 and 886 show the signals provided by the monitor 110 upon the detection of each acceptable respiration pattern (FIG. 1) calculated by moving averages over the last 10 respiration patterns that were found acceptable by procedure 226 (FIG. 2). These signals include respiration period 882, amplitude 884, and the ratio between the respiration period variability and the average period ('relative respiration period variability') 886. In the embodiment depicted in FIG. 8 the trend for each of these three characteristics at any data point was expressed by the sum of the signs of the changes between five consecutive data points. For example, if a series of six consecutive values of a characteristic is given by 4, 5, 6, 12, 15 and 16 the respective differences 1, 1, 6, 3 and 1 are all positive, then the sum of signs is 5 (the maximum value). In contrast, for the series 4, 8, 8, 7, 15, 13 the differences are 1, 0, 1, 2, −2 and the sum of signs is 2, taking zero for a zero difference. According to one implementation, a pre-sleep transition event is characterized by a simultaneous decrease in respiration period and amplitude and an increase of the relative respiration variability ratio, as illustrated by frames 882, 884 and 886, respectively. Such an event can be characterized by the Total Trends Score defined by:

−[trend of respiration period]−[trend of respiration amplitude]+[trend of the relative respiration variability ratio]

Using the expression of trend in terms of the sum of signs, the Total Trends Score expression may vary, in general, between +15 and −15. Frame 888 shows the variation of the Total Trends Score during the time window of 200-800 sec. In this implementation of the invention we define as the pre-sleep transition the first time, at which the Total Trends Score is greater than 12. This happens at about 560 sec at the point 890 marked in frame 888, through which passes the vertical line i. The six points (5 differences) that correspond to the detected pre-sleep transition are connected by lines that appear as features 892, 894 and 896 in frames 882, 884 and 886, respectively. Frame 898 shows the moving average of sync over the last ten consecutive values during the time window of 200-800 sec. The sync values are provided by the sync detector 118 (FIG. 1) via the SNCPAR. In this implementation we define the onset of sleep at the time point, at which that sync average is lower than 40%, marked at about 745 sec in frame 898 by line ii (feature 900). It will be noted that the respiration and its characteristics shown in frames 880, 882, 884 and 886 seem to reach sleep-like respiration at about 700 sec while the user still demonstrates ability to follow the guiding stimulus. This example demonstrates that subjects may display sleep-like respiration while still being awake, and the addition of a low-sync value is important for defining the onset of sleep using respiration data. On the other hand, it can be demonstrated that providing a guiding stimulus after sleep detection that is asynchronous with the user respiration pattern may increase wakefulness in some subjects, who renew sync with the guiding tones after sleep is detected. This problem is characteristically relevant to those subjects who suffer from difficulty in falling asleep and who are naturally more sensitive to changes in the external environment and are an important target audience for products based on the present invention. Possible solutions to this problem are presented below and are an integral part of the present invention. It will be appreciated that the criteria for pre-sleep and sleep detection described by FIG. 8 are only one example aiming to clarify the concepts and other criteria may be useful, as well.

Figure 9:
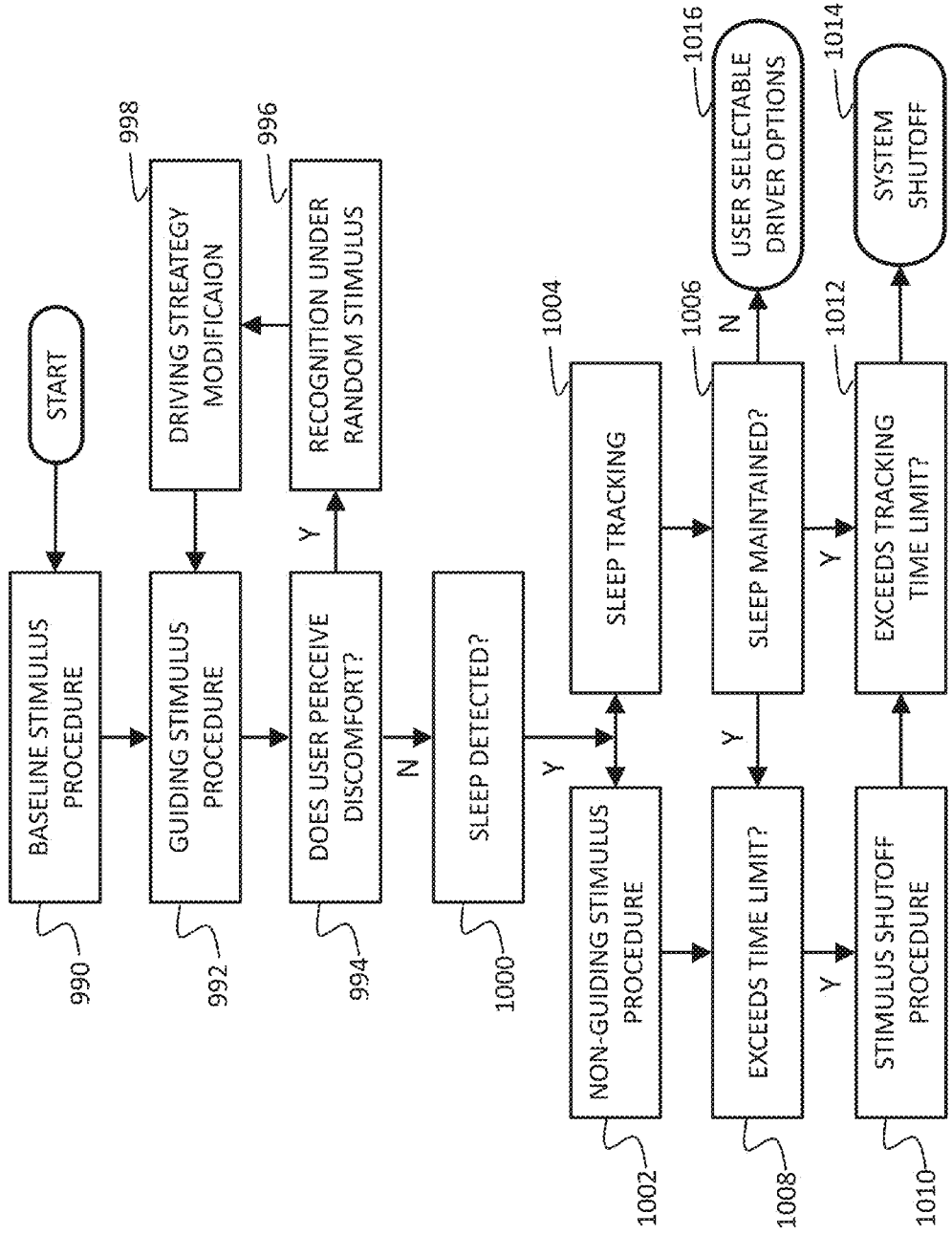
FIG. 9 is a flowchart illustrating schematically the stimulus strategy selection during a typical session controlled by the driver, such as driver 114, employed in the system of FIG. 1, in accordance with an embodiment of the invention.

Reference is now made to FIG. 9, which is a flowchart illustrating schematically a typical structure of a session and the corresponding stimulus strategy as controlled by the driver, such as driver 114, employed in the system of FIG. 1, in accordance with an embodiment of the present invention. In general, the driver 114 determines the stimulus type, structure, pattern characteristics and timing according to the phase of the session and the various signals received from the monitor 110, sync detector 118, sleep detector 120 and operator commands (FIG. 1). For example, when audio stimuli are employed, the nature of the sound pattern and even the identity of a musical composition and its internal structure, as well as its instrumentation, spectral distribution and amplitude may be selected following the operator commands.

Upon starting the session by the user command, the driver activates the stimulus generator 116 (FIG. 1) via the signal DSGPAR to operate according to a Baseline stimulus procedure 990. During this phase the monitor 110 detects the characteristic points (FIG. 2). Since it is essential that user respiration during this phase be natural and unconstrained, the selected stimulus in should preferably have a non-rhythmic nature, i.e. the stimulus should not have any temporal dependency on respiration, e.g. the stimulus may be pre-recorded sounds of sea waves or musical tones generated from stored codes played at random time intervals. In another embodiment, the detection of some or all of characteristic points results in the onset of a stimulus specific to the characteristic point, e.g. high-pitch and low-pitch tones or vibrations upon detecting inspiration and expiration, respectively. In another embodiment, generating a stimulus upon detecting a characteristic point may be limited to one type of characteristic points, e.g. onset of inspiration, but then continues with adding stimulus upon detecting a second characteristic point, e.g. the onset of expiration. This procedure may add some flexibility to the initial variation of the respiration pattern when being entrained by the stimulus. Upon assessing the acceptability of a predetermined number of single respiratory patterns the monitor provides the driver with appropriate notification that is included in the signals MONPAR (FIG. 2). At this point the driver may indicate to the user the successful detection of the respiration pattern, and then activates the guiding stimulus procedure 992 with the purpose of guiding the user to gradually modify at least one temporal characteristic of the user respiration pattern responsive to the monitored respiration characteristics, where the rate of characteristics modification is provided by the driver subject to the user command. In some embodiments such modification may include slowing down respiration rate while increasing the expiration-to-inspiration durations ratio. This type of modification has been demonstrated to reduce neural sympathetic activity. The details of such calculations and the procedure for generating of the onset time for the corresponding stimuli are described according to the technology described in U.S. Pat. Nos. 5,076,281 and 5,800,337 and some of these have been implemented in the RESPeRATE™ device. In case of a music-like audio pattern the preferable technology for composing music that can function as a guiding stimulus for a multiphase respiration pattern is described in U.S. Pat. No. 8,183,453. In another embodiment the variation of the stimulus pattern characteristics that correspond to the respiration temporal characteristics is based on physiological relationships between the respiration characteristics that minimize the user efforts when being guided to slow breathing. Such relationship can be established by dedicated experiments.

The optimal guiding stimulus enables a user to modify the breathing pattern without exerting conscious efforts. However, this may not be the case for some users, for whom synchronizing the respiration pattern to the stimulus pattern may require effort, as the ability to change relative durations of different characteristics, e.g. expiration and inspiration, as a function of the respiration rate is highly individualized. The problem becomes more severe if the user wishes to fall asleep, as the need to exert conscious efforts is counterproductive to falling asleep. In accordance with some embodiments a user, who perceives discomfort associated with effort needed for synchronizing respiration and stimulus patterns, may provide an input (OPC) to the driver 114 (FIG. 1) in order to activate via procedure 994 a corrective action as follows: In response to the (OPC) input, a procedure 996 provides to the stimulus generator 116 a command DSGPAR (FIG. 2) that replaces the generation of the guiding stimulus by that of a non-rhythmic stimulus, e.g. the sounds of ocean and wind, or tones played at random intervals, creating in practice a Pause phase in the guiding phase. During this time the monitor 110 detects the new respiration characteristics similarly to the procedure 990 used for the Baseline phase. When completed, procedure 998 compares the new respiration characteristics determined during the Pause phase with the ones measured at Baseline. If differences exceed a predetermined threshold, procedure 998 may update the rules of respiratory pattern modification used for the guiding phase. Alternatively, the operator may instruct the driver to apply such change of rules only after accumulating enough data from past Pause phases when reaching statistical significance. Alternatively, the individualized guiding rules may be selected by the user (not shown in the scheme).

Upon completion of the procedure 998, the guiding stimulus procedure 992 continues. While the use of the Pause phase, as described by procedures 994 and 996 has already been implemented in the RESPeRATE™ device, the RESPeRATE™ device does not include guiding rules modification, as described by procedure 998.

When the sleep detector 120 indicates to the driver 114 the onset of sleep via signal SLDPAR (FIG. 1), as represented by the decision statement 1000, the driver responds by stopping the guiding stimulus and provides the stimulus generator 116, via DSGPAR (FIG. 1), a definition of non-guiding stimulus using procedure 1002. In accordance with the invention and for reasons that were mentioned previously this non-guiding stimulus is characterized by the following features: a) it is not intended to modify systematically respiration characteristics; b) it has to bear similarity to the guiding stimulus to a level wherein the majority of subjects cannot perceive the transition between the guiding and the non-guiding stimulus, and c) it may have a stabilizing effect on the respiration pattern, if the user still has some ability to sync respiration with the stimulus. In parallel, a sleep tracking procedure 1004 is activated and is operative to determine if respiration continues to be of the type characterizing sleep. As part of this procedure, the driver modifies via signal DMNPAR the thresholds used by the monitor 110 (FIG. 1) for the determination of respiration irregularity in a pre-selected set of respiration single- or multiple-pattern characteristics. The newly calculated irregularity measures are provided by the monitor 110 to the driver 114 via signal MONPAR (FIG. 1). Using a selected set of these measures, procedure 1006 determines if sleep is maintained. It is understandable that sleep maintenance requires low-enough level of respiration irregularity at least shortly after the sleep detection (at later sleep states as REM sleep respiration may become irregular). If sleep is maintained, the non-guiding stimulus procedure 1002 continues until exceeding a pre-selected time limit (decision statement 1008), and then the stimulus shutoff procedure 1010 is activated and preferably reduces in a gradual way the stimulus level down to zero. If the user pre-selects the 'tracking mode' via commands OPC provided to the driver 114 (FIG. 1), the driver keeps the system on during a pre-selected time that is counted from the end of the stimulus shutoff procedure 1010. If the time limit is exceeded (decision statement 1012) the driver shuts off the system (statement 1014). Such time limit may include all night if desired. The pre-selected sleep tracking procedure 1004 may include also a different protocol of data communication between the sensor and the monitor that is controlled by the driver and that may be important for reducing data volume and/or saving energy in the case of a digital respiration sensor energized by a battery. If sleep is not maintained (decision statement 1006), as frequently happens when subjects fall asleep only intermittently or wake up during the night, the driver responds in accordance with selectable operator commands OPC 1016 that may include, for example, not renewing stimulus generation and shutting off the system when tracking time limit is exceeded (procedure 1012); renewing the non-guiding stimulus procedure 1002, if previously shutoff; renewing the guiding stimulus procedure 992; activating a stimulus generation procedure that starts with non-guiding stimulus and changes continuously into a guiding stimulus in response to increasing sync (will be detailed hereafter), and 'freezing' or 'unfreezing' the system operation at any time. The last option is particularly useful when the subject has to stop using the system temporarily, e.g. going to urinate. Manual bi-directional switching between guiding and non-guiding stimulus at any phase of the session is another option for a user, who may find non-guiding stimulus enjoyable and relaxing. However, in this case the algorithms used by sleep detector 120 may require some modification, as described below.

Reference is now made to FIG. 10 that illustrates schematically examples of three different temporal structures of a non-guiding stimulus generated by the driver 114 (FIG. 1). As mentioned previously, structures of non-guiding stimuli according to the invention are not configured to modify respiration characteristics systematically, are hardly perceived by a not-fully-awake user as different from guiding stimuli and may have a stabilizing effect on the respiration pattern in case the user still has some ability to sync with the stimulus. FIG. 10 illustrates schematically a respiration signal with some naturally occurring variability in the temporal respiration characteristics between the patterns, where the stimulus structure is based on detecting the onset of inspiration and expiration (points a and b in FIG. 3, respectively). The temporal structure of the stimuli shown includes the 'inspiration' and 'expiration' stimulus phases (filled and unfilled rectangles, respectively). The time difference between the onsets of the same phase in the respiration and the stimulus pattern indicated by the dashed lines, is represented by filled rectangles marked by '+', if the respiration onset lags after the stimulus onset, and otherwise by '−'. Stimulus A is characterized by the onset of 'inspiration' and 'expiration' stimuli that occur immediately after the detection of points a and b, respectively, in the respiration signal by routine 222 (FIG. 2). In this respect stimulus A is actually a real-time translation of the respiration pattern into a stimulus one. Its advantage is that the stimulus does not display time difference with respect to the user respiration phase, which reduces the chance of waking up the user. On the other hand, sync is meaningless, as its value is 100% by definition and thus cannot provide an indication for wakefulness in case the user wakes up from sleep. In Stimulus B the duration of the 'inspiration' time is a moving average of the monitored inspiration time calculated over the last n acceptable respiration patterns (see procedures 226 and 228 in FIG. 2). In this respect the resulting time difference shown in FIG. 10 between the detected onsets of inspiration and the corresponding 'inspiration' stimulus may not be systematic. The advantage of stimulus B is that it can detect the sync level without trying to modify respiration. Therefore, it enables detection of changes in awareness during sleep tracking (procedure 1004 in FIG. 9) in terms of sync level and thus provides input to the driver regarding activation of the guiding stimulus in case sleep is not maintained and that such an option was selected by the user (procedures 1006 and 1016, respectively, in FIG. 9). If the guiding option was not selected, sync with stimulus B (for inspiration only) enhances the regularity of the respiration pattern. Stimulus C provides the user with 'inspiration' and 'expiration' stimuli based on the last n acceptable respiration patterns and may regularize respiration. However, it may generate a finite time difference between the stimulus and the respiration if the user is unable to sync even partially. In this case the system may apply the shift correction procedure described in U.S. Pat. No. 5,800,337.

Owing to the real-time nature of the stimulus generation in stimuli type A and B some temporal characteristics that belong to patterns that are later classified as unacceptable cannot be eliminated. Therefore, in some embodiments of the invention the composition of non-guiding stimulus of type A for the whole time and for the 'expiration' duration in stimulus of type may include algorithms for handling some aspects of the respiration signal that may be counterproductive to sleep induction or maintenance when transformed into stimuli. For example, some subjects with sleep disordered breathing display temporarily low amplitude respiration movements and even complete cessation of respiration and low amplitude peaks reflecting heart beats, as illustrated by patterns 3 and 4 in FIG. 6. In some embodiments of the invention the onset of a new stimulus phase may require that the time derivative of the respiration signal at the onset point (see parameter P6($n$) in FIG. 3) should exceed an adaptive threshold. This is mainly relevant to the onset of inspiration. If a detected point threshold does not comply with this requirement the stimulus of the last phase (usually expiration) will preferably continue. Another example of such algorithm is providing a minimal duration to the phase after detection of its start in order to avoid short-duration stimulus that may be uncomfortable to the user. It will be appreciated that the presented stimulus types are presented just as examples and other complex stimulus types that correspond to any number of characteristic points can be defined by those who are skilled in the art. Furthermore, the different features of stimuli of types A, B and C suggest that it may be advantageous to change the non-guiding stimulus type according to the state of wakefulness and its tendency to change, as detected by the sync detector 118 (FIG. 1). For example, this may involve starting with stimulus A but switching into B and C if the sleep maintenance indices detect enhanced respiration regularity, alternatively activating the guiding for only one phase of the stimulus, e.g. 'inspiration' for stimulus of the type B, which creates an intermediate case between guiding and non-guiding—all according to a pre-selected or online user selection. Such flexibility may help to assist actively in inducing and maintaining sleep. Finally, in case the user selects manually non-guiding stimulus while being awake and the stimulus type does not enable the determination of sync, e.g. stimulus type A in FIG. 10, the time point of pre-sleep transition detection, which is determined using the respiration pattern characteristics by procedure 772, if accepted as respiration that characterizes sleep by procedure 774 (FIG. 7), may be taken as the sleep detection time. It is to be noted that the description of the non-guiding stimulus according to the invention has been not disclosed previously.

Reference is now made to FIG. 11 that illustrates an implementation of the invention that includes a respiration sensor which communicates with a digital device like mobile phone, iPAD™ or laptop, where the data processing and stimulus generation, as described in the present invention, are controlled by a specialized application ('App'). This embodiment includes a belt-type capacitive respiration sensor 1100, as described in U.S. Pat. No. 7,717,858, that is worn on the abdomen or the chest of a user 1102 and communicates with a mobile phone 1104. Examples of the respiration signal obtained by this sensor are shown in FIGS. 3 and 8. Preferably, this sensor is battery operated and bi-directional data communication is enabled by a wireless Bluetooth low energy (BLE) technology. After registration in a dedicated website and getting an operational code the user 1102 turns on the sensor by pressing a button located on the sensor. After completing the pairing process the respiration signal is sampled typically at 100 ms intervals and transmitted to the mobile phone. The stimulus to the user generated by the mobile phone is preferably audio and is delivered to the user via flat speakers placed under the pillow 1106 (the so-called 'Pillow Speakers') that are connected to the ear jack in the mobile via a cable 1108. Other types of commercially available speakers, e.g. earphones can be used, as well, including ones that can receive the signal wirelessly.

It is appreciated that other types of contact respiration sensors are applicable. A partial list includes piezoelectric films, capacitive-, inductive-, sound-, and flow-based sensors. Non-contact respiration sensors are particularly attractive for being comfortable a user in bed. Such sensors can be placed over- or under the sheet, mattress, pillow or bed. Other types of non-contact respiration sensing involve pressure generated inside fluid-filled cavities in specialized mattresses and pillows, Doppler microwave, infrared light and sounds monitored via microphones, and sensor chips, e.g. micro accelerometers, that are currently integrated into mobile phones and may detect respiration movements if placed on or near the body. It is appreciated that some of these sensors provide signals reflecting also other physiological activities as heart beats and body movements that may be useful for refining the monitoring of the state of the user. It is further appreciated that according to the present invention sensors must identify the onset of at least inspiration and expiration and preferably the onset of two additional phases: post-expiratory pause and breath holding. For some limited applications it is sufficient to identify the onset of one phase only, preferably inspiration.

It is also appreciated that a guiding stimulus other than audio signals can be used. For example, tactile stimulus in the form of vibration and weak electrical current are known in the art to stimulate respiratory muscles and may be used for the guiding process after detecting sleep. Such vibration and currents may be applied via patches placed on the respiratory muscles and can be an integral part of the belt sensor or under-the-sheet type of respiration sensor, where the operation of these units is controlled by the App and the power source depends on desired configuration.

FIG. 11b illustrates an example of a screen for guiding phase 1110, which is one of the screens generated in an embodiment of the App installed in the mobile phone 1104 (FIG. 11a). The screen provides visualization of the monitored respiratory signal using an avatar 1112, in which the respiratory movements are represented by dynamic filling of an empty space 1114 by stripes 1116, the number of which increases from one, at the onset of inspiration, reaching a maximum at the end of inspiration and decreasing to zero during expiration. This avatar mirrors to the user the state of lung filling in real time. The stimulus, which is musical tones in this case, is represented by a 'background filling domain' 1118 with dynamic borderline 1120 that increases from the bottom of the screen (onset of 'inspiration' stimulus) to a limiting curve 1122, at the end of 'inspiration', and moves downward during 'expiration'. The respiration signal itself 1124 is plotted in real time, where the 'now' point 1126 is marked at its right end. Synchronization between respiration movements and the guiding tones requires sync between the features presenting both processes, which is easy to perceive. The displayed respiration rate 1128 and the sync level 1130 may represent, for example, averages taken over the last three acceptable respiration patterns. In order to avoid unnecessary visual load, which can be counterproductive to falling asleep, the guiding screen 1110 may be displayed to the user only when guiding visualization is needed, subject to user selection. An additional feature not shown in FIG. 11b for simplicity is the accumulated time spent by the user in 'good performance', as defined by breathing at rate below 10 breaths/min and sync greater than 60%, represented by circular segments that surround the sync 1130, where each represents one accumulated minute of good performance. This feedback has been found important for users when awake and has been shown to be associated with clinical benefits (Gavish B, "*Device-guided breathing in the home setting: Technology, performance and clinical outcomes*", Biol. Psychol. 2010; 84:150-156).

FIG. 11c illustrates a simplified example of a Sleep-Report screen 1132, which is one of the screens generated in some embodiments of the App installed in the mobile phone 1104 (FIG. 11a). The screen is presented to the user after waking up in the morning. The 'nightline' bar 1134 extends from the start of the session (top) and ends at waking up (bottom), where the waking-up time is inserted by user manually in After-Sleep-Questionnaire (ASQ) screen (not shown), which may also be set automatically by an alarm clock included in the App. The bar also includes the minutes to fall asleep (feature 1136), i.e. time-to-sleep, as detected by the sleep detector 120 (FIG. 1). The time spent in being awake after falling asleep Make ups') is estimated by the user and inserted in the ASQ screen, but can also be estimated by the App if sleep tracking procedure 1104 (FIG. 9) is selected by the user for the whole night. Using these data the 'in bed time' (time from turning on the application to waking up minus 'wake ups') and the 'sleep time' can be determined. The 'woke up feeling' is inserted by the user in the ASQ screen and is selected from a given series of descriptive scoring. The chart 1138 illustrates the pattern-by-pattern variation of the average respiration rate over the session, e.g. average over last three acceptable respiration patterns provided by the monitor 110 in FIG. 1. This plot is similar to the plot 882 in FIG. 8, if the respiration period is replaced by respiration rate. The moment of sleep detection is marked by an arrow 1160 (its value is shown by feature 1136).

It is appreciated that the mobile screens illustrated in FIGS. 11b and 11c are just possible examples of multiple screens that present the best mode of implementation according to the present invention.

It is further appreciated that the Sleep Report may include more complex scenarios as repeated sessions and reference to events that occurred during the sleep reported either manually at the ASQ screen or detected automatically when the tracking mode is activated, e.g. activation of the guiding phase in case of displaying a tendency to wake up. Such information and related ones may provide additional input for more objective evaluation of the sleep quality.

The App may include a Before-Sleep-Questionnaire (BSQ) for documenting pre-sleep activities that may be important for improving sleep habits and may be important covariates in understanding the outcomes of prolonged use of the system.

In this implementation both raw, analyzed data and questionnaires can be uploaded to and retrieved from a server for generating a statistical and/or detailed summary of multi-session reports, if selected by the user, useful for evaluating efficiency of the intervention and changes in the sleep habits. Furthermore, users may share data and reports if desired.

Although the invention focuses on sleep induction and maintenance it is appreciated that one of its byproducts is monitoring and analyzing respiration structure during sleep that may be important for other applications.

It will also be understood that while the invention has been described in terms of the functionality of interconnected discrete units, the system according to the invention may be a suitably programmed computer. To the extent that to all intents and purposes, a smartphone, PDA, tablet and other similar hand-held devices are basically programmable processors in a self-contained device they too may be used to implement the invention in response to a sensor signal indicative of the user's breathing. Likewise, in such cases, since such devices also have a communications interface the sensor may be remote from the processor and may send the sensor signals wirelessly, for example, typically over the Internet to a remote monitoring unit where the processing is carried and in response to which the stimulation signal is derived and fed back, also typically wirelessly, typically over the Internet to the user via a smartphone or other similar hand-held device.

Likewise, the invention contemplates a computer program being readable by a computer for executing the method of the invention. The invention further contemplates a machine-readable memory tangibly embodying a program of instructions executable by the machine for executing the method of the invention.

It is also to be noted that while various distinctions of the invention over the prior art such as the RESPeRATE™ device have been mentioned, these distinctions are not to be construed as the only distinctions over the prior art.

It will be appreciated by persons skilled in the art that the present invention is not limited by what has been particularly shown and described hereinabove. Rather the scope of the present invention is defined only by the claims which follow.

I claim:

1. A system for sleep induction, detecting and tracking comprising:
   a monitor coupled to a respiration sensor configured to analyze a respiration signal and to derive respective characteristics from both single- and multiple-respiration patterns of a user;
   a stimulus generator configured to provide multiple guiding stimuli and multiple non-guiding stimuli to the user, each guiding stimulus of the multiple guiding stimuli and each non-guiding stimulus of the multiple non-guiding stimuli bearing at least one selectable time-relationship with a respective selected temporal characteristic of said single- and multiple-monitored respiration patterns of a user, wherein each of said guiding stimuli is operative to change at least one of said temporal characteristics of the respiration patterns by synchronization of respective respiration movements of the user with specific aspects of said guiding stimuli;
   a sync detector configured to determine at least one measure of synchronization expressed as a function of a time lag between at least one of said selected temporal characteristics of selected ones of said guiding stimuli and a corresponding one of the selected temporal characteristics of the respiration patterns for each respiration pattern and for using the at least one measure of synchronization to determine a performance indicator identifying an extent of the user to follow the guiding stimuli;
   a sleep detector configured to be responsive to signals provided by the monitor and to the performance indicator provided by the sync detector for indicating the onset of sleep; and
   a driver configured to be operative to continuously control operation of the stimulus generator,
   the sync detector and the sleep detector based on signals as they are received from at least the sync detector, the sleep detector and the monitor, during the operation of the monitor,
   wherein the non-guiding stimuli are operative to maintain the temporal relationships with the respective selected temporal characteristics of said single- and multiple-monitored respiration patterns of the user without modifying said temporal characteristics of the respiration patterns.

2. The system according to claim 1, wherein the driver is further operative to control the operation of the monitor.

3. The system according to claim 1, wherein the driver is responsive to one or more user commands for controlling the operation of the stimulus generator.

4. The system according to claim 3, wherein the driver is operative to the user commands, and the user commands are predetermined or received while providing the multiple guiding stimuli and the multiple non-guiding stimuli to the user.

5. The system according to claim 4, wherein the driver is responsive to a change in respiration characteristics in response to a user-initiated pause in operation of the stimulus generator.

6. The system according to claim 5, wherein:
   the driver is responsive to a user command indicative of user discomfort associated with effort needed for synchronizing respiration and stimulus patterns for causing the stimulus generator to generate a non-rhythmic stimulus creating a pause phase in a guiding phase.

7. The system according to claim 6, wherein:
   the monitor detects new respiration characteristics during the pause phase and compares the new respiration characteristics with baseline characteristics, and the monitor updates the time-relationships for the guiding phase if differences between the new respiration characteristics and the baseline characteristics exceed a predetermined threshold.

8. The system according to claim 6, wherein the driver is responsive to manual user commands to apply a change of rules after accumulating enough data from past Pause phases when reaching statistical significance.

9. The system according to claim 1, wherein the sleep detector is configured to determine the onset of sleep based on a score that peaks when all selected trends of the selected temporal characteristics provided by the monitor display a desired trend and the performance indicator decreases below a predetermined threshold.

10. The system according to claim 1, wherein the non-guiding stimuli are selected to respond in real time, or nearly real time, to at least one of said selected temporal characteristics of the respiration patterns.

11. The system according to claim 1, wherein:
    the monitor determines if sleep is maintained;
    the driver is responsive to sleep being maintained to shutoff the guiding stimuli and invoke the non-guiding stimuli for a predetermined time period.

12. The system according to claim 11, wherein:
    the driver is configured to keep the system on during a pre-selected time that is counted from when the guiding stimulus are shutoff, and
    the driver is configured to shut off the system if the pre-selected time limit is exceeded.

13. The system according to claim 11, wherein the driver is responsive to a user command for switching between guiding stimuli and the non-guiding stimuli.

14. The system according to claim 1, wherein the driver is configured to modify characteristics of the respiration signal that are counterproductive to sleep induction or maintenance.

15. The system according to claim 1, wherein the at least one measure of synchronization serves as a metric of user awareness.

16. The system according to claim 1, being a standalone device.

17. The system according to claim 1, being a suitably programmed portable device that is configured to receive respiration data from a sensor connected directly or wirelessly thereto.

18. The system according to claim 17, wherein the portable device is configured to process the respiration data and generate the multiple guiding stimuli as musical tones provided to the user via earphones or speakers and further to generate audiovisual stimuli via a mobile user interface.

19. The system according to claim 17, wherein the portable device is further configured to obtain and analyze the respiration signal and the respective characteristics from both single- and multiple respiration patterns of the user and provide reports regarding performance, and warnings with corrective messages.

20. The system according to claim 1, wherein the guiding stimuli comprise a tactile stimuli.

21. The system according to claim 20, wherein the tactile stimuli are is applied via patches placed on the respiratory muscles.

22. The system according to claim 20, wherein the tactile stimuli comprise mechanical vibrations or weak electrical currents used to stimulate the respiratory muscles.

23. The system according to claim 1, wherein the selected temporal characteristics include moving averages of single- or multiple pattern characteristic; trends; variability between two successive characteristics in a continuous or dichotomous form; variability within multiple successive patterns, and variables characterizing recurrent groups of multiple-patterns.

24. The system according to claim 1, wherein:
the sync detector comprises a trigger matching unit that receives from the monitor a first trigger signal that marks the detection time of characteristic points and receives from the driver a second trigger signal that marks the timing of corresponding stimuli to the user;
the trigger-matching unit is adapted to assess the validity of one-to-one correspondence between events marked by the first and second trigger signals; and
the sync detector is configured to ignore characteristic points for which said one-to-one correspondence is not possible.

25. The system according to claim 1, wherein the driver is responsive to sleep not being maintained and for controlling the operation of the stimulus generator according to one or more of the group consisting of:
renewing a first procedure regarding the guiding stimuli,
not renewing generation of the guiding stimuli and non-guiding stimuli and shutting off the system within a predetermined time limit,
renewing a second procedure regarding the non-guiding stimuli if previously shutoff,
renewing the guiding stimulus procedure,
activating a stimulus generation procedure that starts with the non-guiding stimuli and changes continuously into the guiding stimuli in response to increasing sync, freezing system operation, and unfreezing system operation.

26. The system according to claim 1, wherein said multiple-respiration patterns consist of two or more constituent single-respiration patterns and wherein the respective characteristics derived from said multiple respiration patterns express variability in the respective characteristics derived therefrom, and wherein the respective characteristics derived from both single- and multiple-respiration patterns further include trends relating to changes in the respective characteristics derived from both single- and multiple-respiration patterns over time.

27. A computer-implemented method for sleep induction, detection and tracking comprising:
monitoring and computer analyzing monitored single- and multiple-respiration patterns of a user;
providing under control of the computer to the user multiple guiding stimuli and multiple non-guiding stimuli, each guiding stimulus and each non-guiding stimulus bearing at least one selectable time relationship with a respective selected temporal characteristic of said single- and multiple-monitored respiration patterns, where each of said guiding stimuli is operative to change at least one of said selected temporal characteristics of the respiration patterns during analysis of the respiration patterns of the user by synchronization of respective respiration movements of the user with specific aspects of the guiding stimuli;
determining at least one measure of synchronization expressed as a function of time lag between at least one of said temporal characteristics of selected ones of said guiding stimuli and a corresponding one of the selected temporal characteristics of the respiration for each respiration pattern;
using the at least one measure of synchronization to determine a performance indicator identifying an extent of the user to follow the guiding stimuli;
detecting an onset of sleep based on said monitored respiration patterns, the performance indicator and the at least one measure of synchronization; and
continuously controlling the guiding stimuli and the non-guiding stimuli under control of the computer based on respective current signals relating to at least the at least one measure of synchronization, detection of the onset of sleep and the monitored respiration patterns; and
stopping the guiding stimuli and invoking the non-guiding stimuli following detection of the onset of sleep;
wherein the non-guiding stimuli are operative to maintain the temporal relationships with the respective selected temporal characteristics of said single- and multiple-monitored respiration patterns of the user without modifying said temporal characteristics of the respiration patterns.

28. The method according to claim 27, further including controlling said monitoring.

29. The method according to claim 27, wherein controlling the guiding stimuli and the non-guiding stimuli is further dependent on one or more operator commands.

30. A non-transitory computer-readable memory storing data representative of computer program code, which when run on a computer processor performs the method of claim 27.

31. The method according to claim 27, wherein said multiple-respiration patterns consist of two or more constituent single-respiration patterns and wherein the respective characteristics derived from said multiple respiration patterns express variability in the respective characteristics derived therefrom, and wherein the respective characteristics derived from both single- and multiple-respiration patterns further include trends relating to changes in the respective characteristics derived from both single- and multiple-respiration patterns over time.

* * * * *